(12) United States Patent
Nett et al.

(10) Patent No.: US 10,300,304 B2
(45) Date of Patent: May 28, 2019

(54) SAFETY DOSE INTERLOCK FOR CHARGED PARTICLE BEAMS

(71) Applicant: Pyramid Technical Consultants Inc., Lexington, MA (US)

(72) Inventors: William P. Nett, Waltham, MA (US); John Gordon, Henfield (GB); Raymond Paul Boisseau, Waltham, MA (US)

(73) Assignee: Pyramid Technical Consultants Inc., Lexington, MA (US)

( * ) Notice: Subject to any disclaimer, the term of this patent is extended or adjusted under 35 U.S.C. 154(b) by 0 days.

(21) Appl. No.: 15/904,571

(22) Filed: Feb. 26, 2018

(65) Prior Publication Data

US 2018/0289984 A1 Oct. 11, 2018

Related U.S. Application Data

(60) Provisional application No. 62/481,895, filed on Apr. 5, 2017.

(51) Int. Cl.
*H01J 37/244* (2006.01)
*A61N 5/00* (2006.01)
*A61N 5/10* (2006.01)
*H01J 37/24* (2006.01)

(52) U.S. Cl.
CPC ......... *A61N 5/1064* (2013.01); *A61N 5/1071* (2013.01); *H01J 37/243* (2013.01); *H01J 37/244* (2013.01); *A61N 2005/1087* (2013.01); *H01J 2237/2485* (2013.01); *H01J 2237/24564* (2013.01)

(58) Field of Classification Search
CPC ............... A61N 5/1064; A61N 5/1071; A61N 2005/1087; H01J 37/243; H01J 37/244; H01J 2237/24564; H01J 2237/2485
USPC ........................................... 250/492.1, 492.3
See application file for complete search history.

(56) References Cited

U.S. PATENT DOCUMENTS

| | | | |
|---|---|---|---|
| 9,427,599 B1 * | 8/2016 | Boisseau | A61N 5/1048 |
| 2004/0264626 A1 * | 12/2004 | Besson | A61B 6/032 |
| | | | 378/4 |
| 2013/0231516 A1 * | 9/2013 | Loo | A61N 5/1065 |
| | | | 600/1 |
| 2018/0164445 A1 * | 6/2018 | Sacchi | G01T 1/17 |
| 2018/0243586 A1 * | 8/2018 | Ramezanzadeh Moghadam | |
| | | | A61N 5/1071 |

* cited by examiner

*Primary Examiner* — Nicole M Ippolito
(74) *Attorney, Agent, or Firm* — Intrinsic Law Corp.

(57) ABSTRACT

An assembly for preventing an overdose of a charged particle beam during therapy to a patient includes a pixelated detector apparatus and a controller. The controller includes, for each pixel: a current integrator circuit that converts the local measured current into a total local detected charge integrated from a start time, the integrator circuit outputting an integrator voltage that corresponds to the total local detected charge; and a discriminator circuit that compares the integrator voltage with a reference voltage, the reference voltage corresponding to a maximum acceptable dose for the patient. A logic circuit generates an overdose fault signal if, at any of the pixels, the integrator voltage is higher than the reference voltage.

20 Claims, 8 Drawing Sheets

SAFETY DOSE INTERLOCK FOR CHARGED PARTICLE BEAMS

RELATED APPLICATIONS

The present application claims priority to U.S. Provisional Application No. 62/481,895, filed on Apr. 5, 2017, entitled "Safety Dose Interlock for Charged Particle Beams," which is hereby incorporated by reference.

TECHNICAL FIELD

The present application relates generally to safety controls in charged particle therapy systems.

BACKGROUND

FIG. 1 illustrates a known pencil beam proton therapy system (PBS) 10. The PBS 10 includes a proton beam source 100, beamline apparatus 110, beam detection apparatus 120, scan nozzle 130, and controller 140. In operation, proton beam source 100 generates a proton beam 101 at a requested energy level. The proton beam 101 is then trimmed and/or deflected by electromagnets in beamline apparatus 110. After passing through beamline apparatus 110, the proton beam 101 passes through beam detection apparatus 120, which can measure the location and intensity of the proton beam 101. The proton beam 101 then passes through scan nozzle 130, which includes electromagnets to deflect the beam to target locations in a patient, as represented by isocenter plane 150.

To avoid over-exposing the patient to proton beam 101, the controller 140 uses information from beam detection apparatus 120 to perform real-time calculations of the patient's exposure at defined volume elements or voxels in the patient. These real-time calculations rely on the measured position of proton beam 101, the measured intensity of proton beam 101, the beam energy (which determines the depth of exposure), and the exposure time at each measured position or voxel. As can be seen, these calculations require significant processor power to complete. In addition, the calculations rely on relatively complex software. Such software is expensive to develop and is subject to strict FDA regulations for medical devices.

It would be desirable to overcome one or more of the problems described above.

SUMMARY

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure will be set forth in the following detailed description of the disclosure when considered in conjunction with the drawings.

An aspect of the invention is directed to an assembly for preventing an overdose of a charged particle beam during therapy to a patient, comprising: a detector apparatus comprising detector elements that form a plurality of pixels, the detector apparatus configured to output, for each said pixel, a local measured current corresponding to a local measured intensity of said particle beam at said pixel; The assembly further comprises a controller in communication with said particle beam generator and said detector apparatus. The controller comprises, for each said pixel: a current integrator circuit that converts said local measured current into a total local detected charge integrated from a start time, the integrator circuit outputting an integrator voltage that corresponds to said total local detected charge; and a discriminator circuit that compares the integrator voltage with a reference voltage, the reference voltage corresponding to a maximum acceptable dose for said patient. The assembly also includes a logic circuit that generates an overdose fault signal if, at any of said pixels, said integrator voltage is higher than said reference voltage.

Another aspect of the invention is directed to an assembly for preventing an overdose of a charged particle beam during therapy to a patient. The assembly comprises a detector comprising detector elements that form a plurality of pixels, the detector apparatus configured to output, for each said pixel, a local measured current corresponding to a local measured intensity of said particle beam at said pixel. The assembly also comprises a controller in communication with said particle beam generator and said detector apparatus. The controller comprises, for each said pixel, a current integrator circuit that converts said local measured current into a total local detected charge integrated from a start time, the integrator circuit outputting an integrator voltage that corresponds to said total local detected charge; a first discriminator circuit that compares the integrator voltage with a first reference voltage corresponding to a first maximum acceptable dose for said patient; a programmable reference voltage source that outputs a programmable reference voltage corresponding to a second maximum acceptable dose for said patient; and a second discriminator circuit that compares the integrator voltage with the programmable reference voltage. The assembly also comprises a logic circuit that generates an overdose fault signal if, at any of said pixels, said integrator voltage is higher than the first reference voltage or the programmable reference voltage.

Another aspect of the invention is directed to a method for preventing an overdose of a charged particle beam during therapy to a patient. The method comprises passing the charged particle pencil beam through a pixelated ion detector chamber comprising detector elements that form a plurality of pixels. The method also comprises, for each said pixel: receiving a local measured current collected at said pixel; passing said local measured current through a current integrator circuit that converts said local measured current into an integrator voltage that corresponds to a total local detected charge integrated from a start time; comparing the integrator voltage with a reference voltage that corresponds to a maximum acceptable dose for said patient; and stopping the therapy if the integrator voltage is greater than the reference voltage.

BRIEF DESCRIPTION OF THE DRAWINGS

For a fuller understanding of the nature and advantages of the present invention, reference is made to the following detailed description of preferred embodiments and in connection with the accompanying drawings, in which.

DETAILED DESCRIPTION

Figure 1:
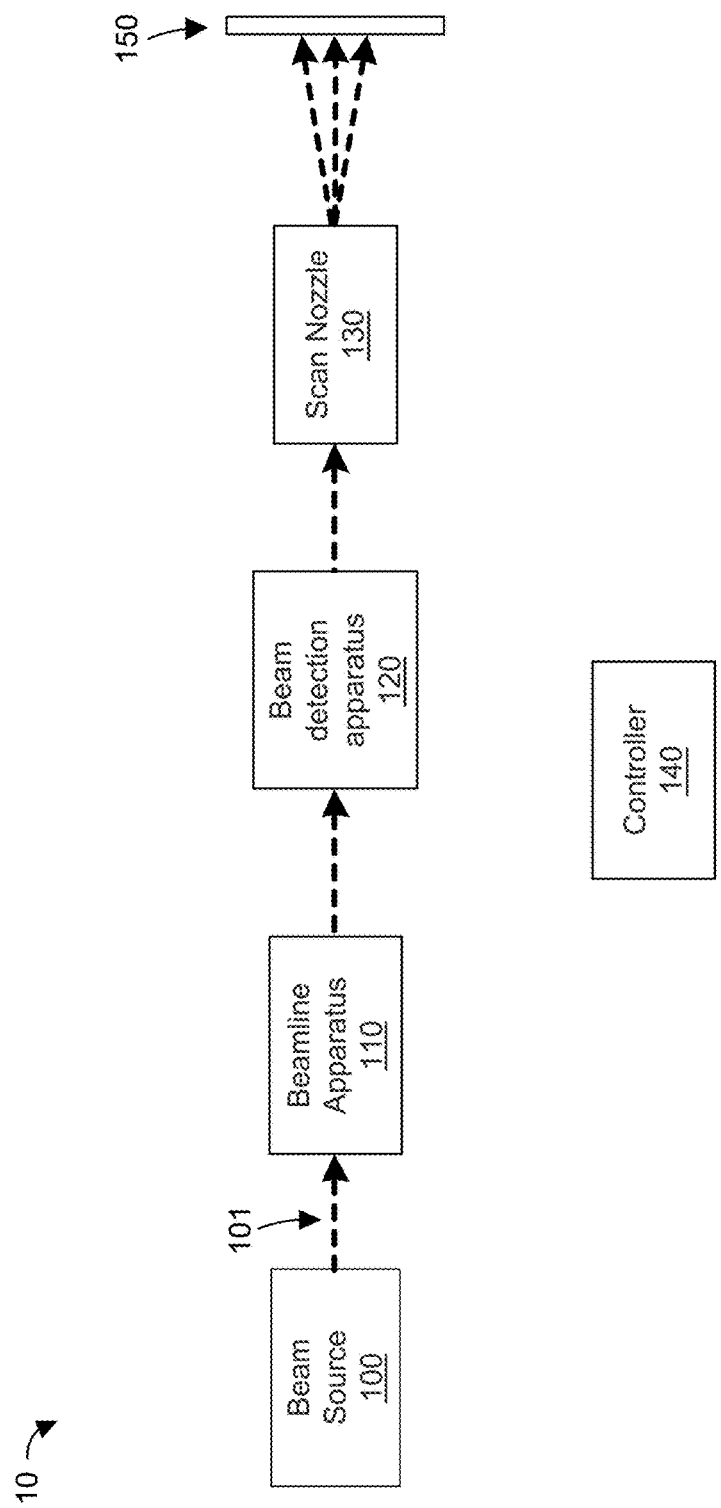
FIG. 1 illustrates a known pencil beam proton therapy system.
Figure 2:
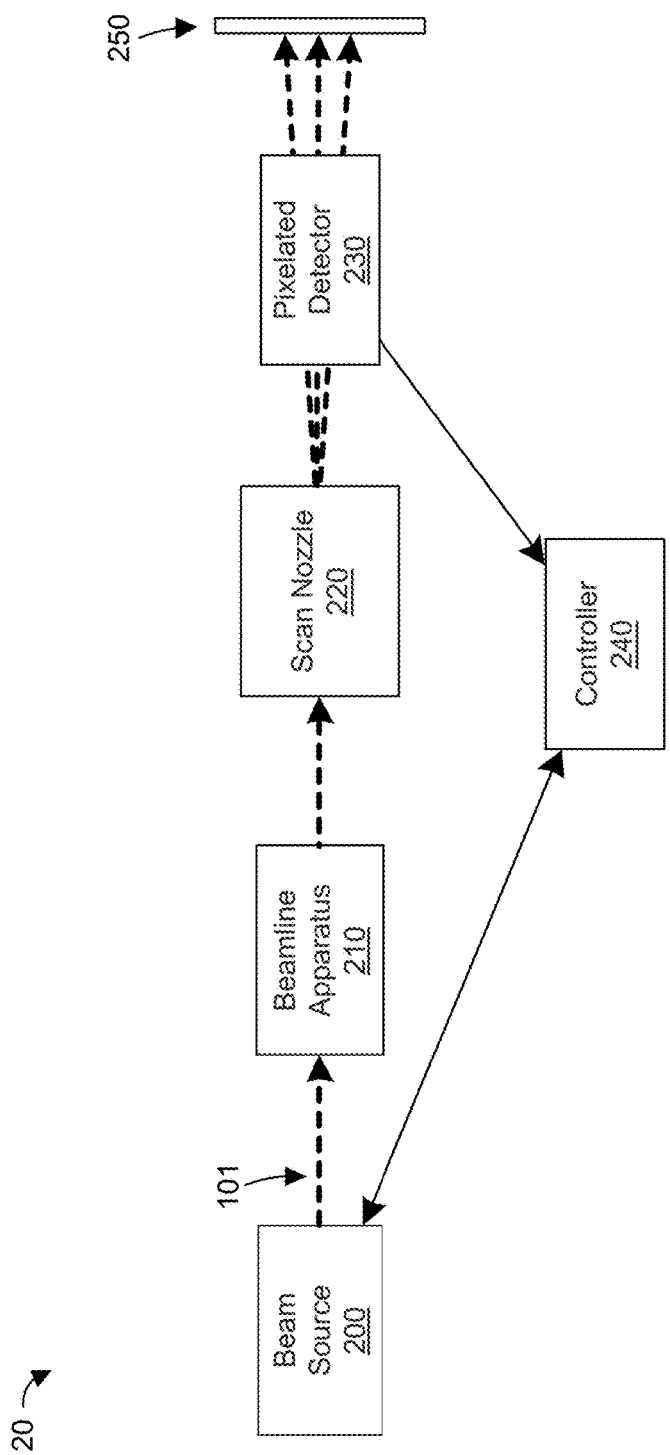
FIG. 2 illustrates a pencil beam proton therapy system according to one or more embodiments.

FIG. 2 illustrates a pencil beam proton therapy system (PBS) 20 according to one or more embodiments. The PBS 20 includes a proton beam source 200, beamline apparatus 210, scan nozzle 220, pixelated ion detection chamber 230, and controller 240. Proton beam source 200. In operation, proton beam source 200 generates a proton beam 201 at a requested energy level. The proton beam 201 is then trimmed and/or deflected by electromagnets in beamline apparatus 210. After passing through beamline apparatus 210, the proton beam 201 passes through scan nozzle 220, which includes electromagnets to deflect the beam 201 to target locations in a patient, as represented by isocenter plane 250. After the beam 201 exits the scan nozzle 220, it passes through pixelated ion detection chamber 230, disposed between scan nozzle 220 and isocenter plane 250. The pixelated ion detector chamber 230 includes detector elements that define a plurality of pixels to collect a current formed when the beam 201 creates ion-electron pairs in an adjacent gas gap within pixelated ion detector chamber 230. The location of the pixels that collect current indicates the position of the beam 201 in the plane of the pixelated ion detector chamber 230. Pixelated ion detector chamber 230 has sufficient lateral dimensions so that it spans the entire scan area, which can be about 30 cm by about 40 cm at isocenter plane 250. Since the pixelated ion detector chamber 230 is disposed at an intermediate point between scan nozzle 220 and isocenter plane 250, the pixelated ion detector chamber 230 can be smaller than the scan area at isocenter plane 250. For example, the pixelated ion detector chamber 230 can be about 26 cm by about 20 cm. In some embodiments, the pixelated ion detector chamber 230 has uniform size pixels. In one example, the pixel size matches or approximately matches the dimensions of the beam spot of beam 201. For example, a typical Gaussian beam with a 5 mm sigma, +/−2 sigma leads to a 20 mm pixel dimension. The pixel dimension can be reduced by the effective magnification of the system, typically about 1.5, resulting in a 12 mm by 12 mm pixel. To cover the scan area, a pixel array of 20×25 can be used, each pixel 12 mm by 12 mm. This would result in ion detector chamber with dimensions of 24 cm by 30 cm. In other embodiments, pixelated ion detector chamber 230 has pixels of non-uniform size. It is noted that the pixel and detection chamber sizes are provide for sake of illustration and are not intended to be limiting.

The magnitude of the current collected at each pixel divided by the area of the pixel is the local beam current density measured at that pixel. The local integrated charge at each pixel (i.e., local beam current density integrated over time) closely corresponds to the dose delivered to the patient at a location in the isocenter plane 250 corresponding to the location of such pixel in the plane of the pixelated ion detector chamber 230. The controller 240 includes a plurality of circuits that compare, for each pixel, the local integrated charge with a maximum charge corresponding to a maximum acceptable dose (e.g., 4 Gray) to the patient. If the local integrated charge exceeds the maximum acceptable dose at any pixel, the controller 240 shut downs beam source 200 to prevent radiation overdose to the patient.

Figure 3:
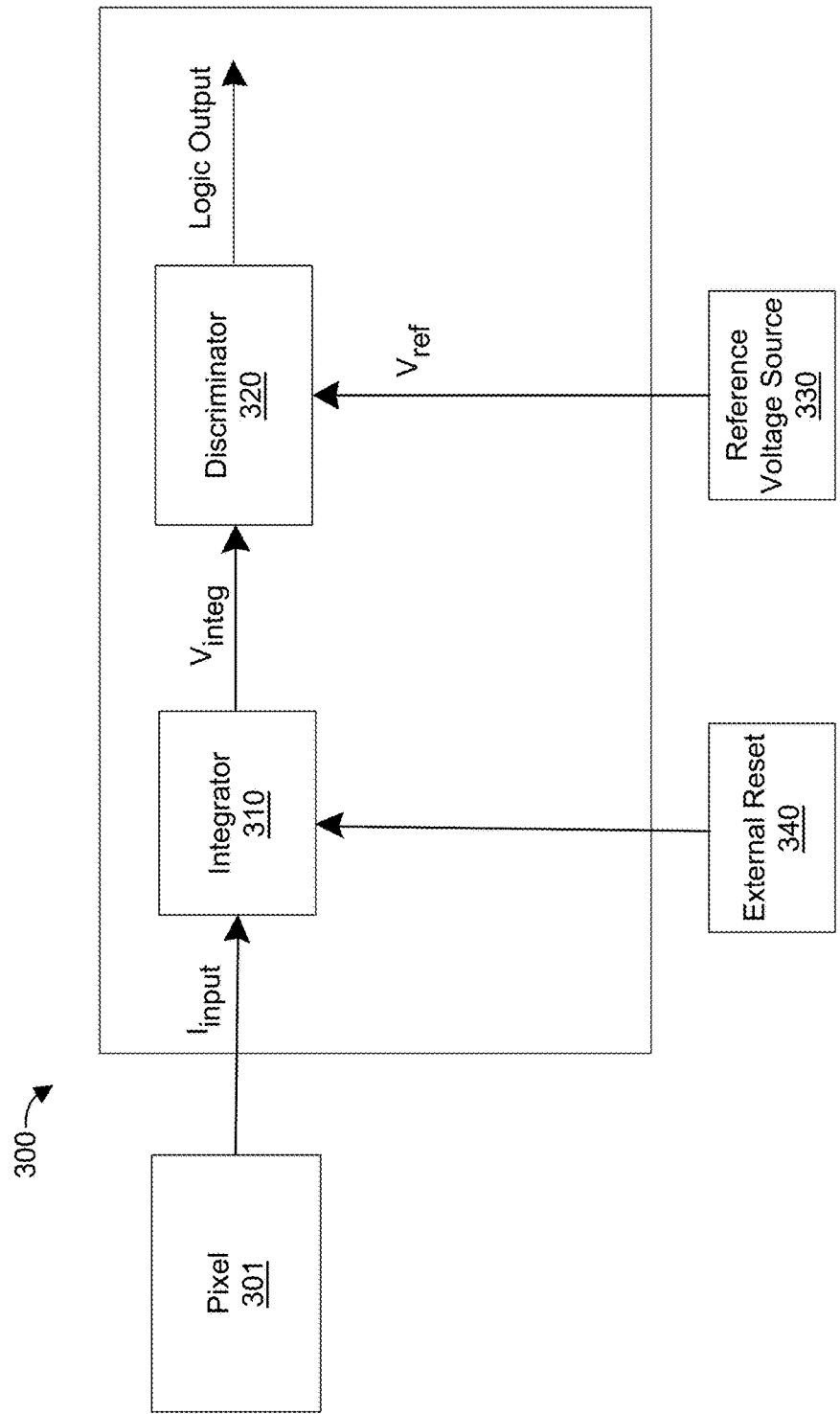
FIG. 3 illustrates an example of a circuit that compares, for a representative pixel, the local integrated charge with a maximum charge corresponding to a maximum acceptable dose to the patient.

An example of a circuit 300 that compares, for a representative pixel, the local integrated charge with a maximum charge corresponding to a maximum acceptable dose to the patient is illustrated in FIG. 3. Circuit 300 includes a current integrator 310 and a discriminator 320. The current integrator 310 receives an input current $I_{input}$ collected by representative pixel 301 in pixelated ion detector chamber 230. The current integrator 310 integrates the input current $I_{input}$ starting from an appropriate start time (e.g., start of treatment or start of treatment at a given energy level), which can be set by external reset 340. The output of the current integrator 310 is an integrated voltage $V_{integ}$ that is proportional to the total charge collected by pixel 301 since the start time. The total charge collected by pixel 301 correlates with the radiation dose administered to the patient at a location in the isocenter plane 250 corresponding to the location of the pixel 301 pixel in the plane of the pixelated ion detector chamber 230.

Discriminator 320 compares integrated voltage $V_{integ}$ with a reference voltage $V_{ref}$ output by reference voltage source 330. The reference voltage $V_{ref}$ corresponds to the maximum acceptable dose to the patient. The maximum acceptable dose can be the maximum acceptable total dose, such as 4 Gray, or the maximum acceptable dose for a given beam energy level. The discriminator 320 outputs a logical output (e.g., a one or a zero) depending on whether $V_{integ}$ exceeds $V_{ref}$. The logical output can be used to send a signal (e.g., via a relay) to shut down beam source 200 to prevent radiation overdose to the patient.

As discussed, FIG. 3 also illustrates an external reset 340 in communication with integrator 310. The external reset 340 sends a signal to current integrator 310 to reset the integration to zero, for example at the start of the therapy or at the start of each beam energy level.

Figure 4:
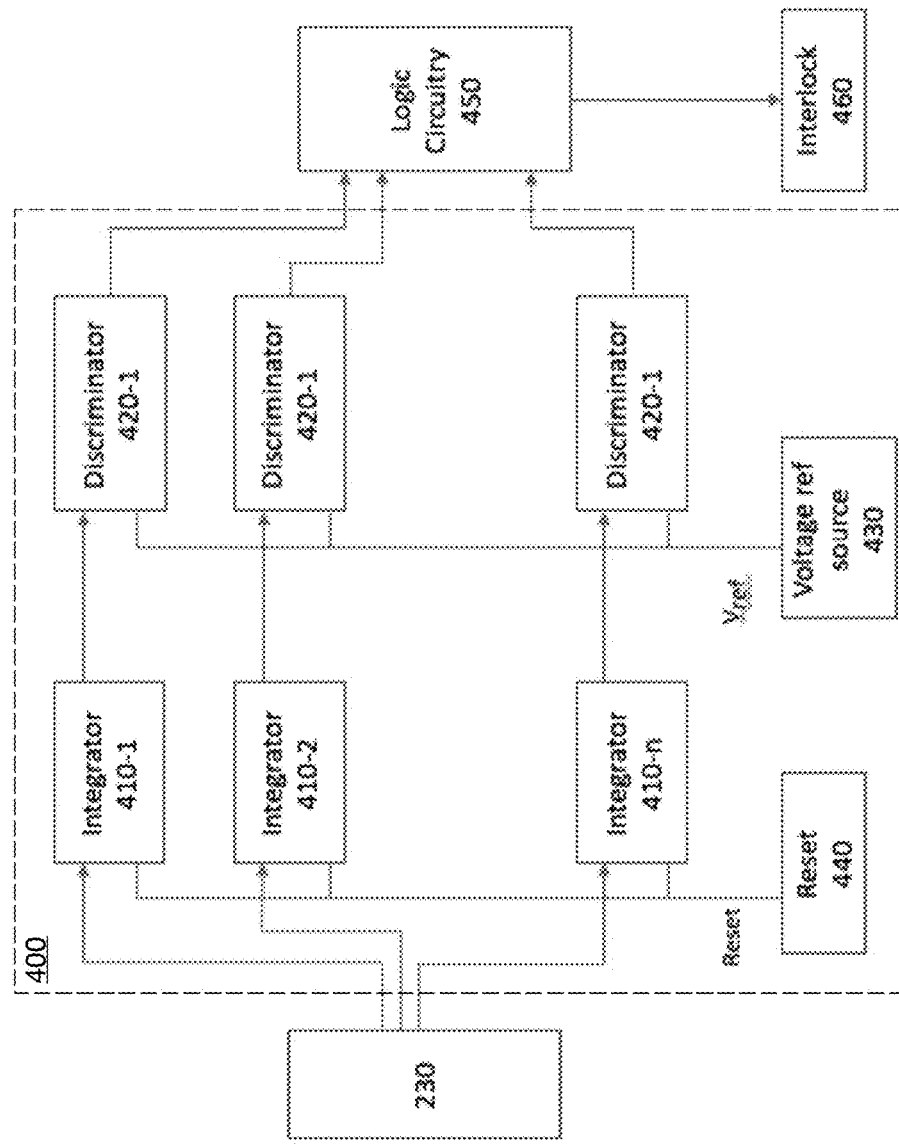
FIG. 4 illustrates control circuitry for preventing patient overdose according to one or more embodiments.

FIG. 4 illustrates control circuitry 40 for preventing patient overdose according to one or more embodiments. As illustrated, control circuitry 40 includes a plurality of similar or substantially identical circuits 400-1, 400-2, . . . , 400-n (in general circuits 400). Circuit 400-1 includes an integrator 410-1 and a discriminator 420-1. Circuit 400-2 includes an integrator 410-2 and a discriminator 420-2. Circuit 400-n includes an integrator 410-n and a discriminator 420-n. In general, each circuit 400 includes an integrator 410 and a discriminator 420, which are the same or similar to integrator 310 and discriminator 320 described above. Each circuit 400 is electrically connected to a pixel in pixelated ion detector chamber 230 via readout cable 401, and there is a separate circuit 400 for each pixel. Thus, if pixelated ion detector chamber 230 includes 64 pixels, control circuitry 40 includes 64 circuits 400.

Each circuit 400 operates in the same or a similar way as circuit 300 described above. For example, each circuit 400 receives an input current ($I_{input-1}$, $I_{input-2}$, $I_{input-n}$) (in general $I_{input}$) collected by a corresponding pixel in pixelated ion detector chamber 230. Integrator 410 integrates the input current $I_{input}$ from a given start time, which can be reset by a reset signal from external reset 440. Circuitry electrically connects the external reset 440 in parallel with each integrator 410, such that the reset signal is sent to each integrator 410 at the same or substantially the same time. The output of each integrator 410 is an integrated voltage ($V_{integ-1}$, $V_{integ-2}$, $V_{integ-n}$) (in general $V_{integ}$) that is proportional to the total charge collected by the corresponding pixel integrated from an appropriate start time (e.g., start of treatment or start of treatment at a given energy level). As discussed above, the total charge collected by each pixel correlates with the radiation dose administered to the patient at a location in the isocenter plane 250 corresponding to the location of the pixel in the plane of the pixelated ion detector chamber 230.

Each discriminator 420-1, 420-2, 420-*n* (in general 420) compares the integrated voltage $V_{integ}$ with a reference voltage $V_{ref}$ output by reference voltage source 430. The reference voltage $V_{ref}$ corresponds to the maximum acceptable dose to the patient. The maximum acceptable dose can be the maximum acceptable total dose, usually 4 Gray, or the maximum acceptable dose for a given beam energy level. Circuitry electrically connects reference voltage $V_{ref}$ in parallel with each discriminator 420, such that each integrator discriminator 420 receives reference voltage $V_{ref}$ as an input. In an alternative embodiment, at least some of the discriminators 420 receive different reference voltages as inputs. Each discriminator 420 outputs a logical output (e.g., a one or zero) depending on whether $V_{integ}$ exceeds $V_{ref}$.

Logic circuitry 450 receives the logical outputs from each discriminator 420 and determines whether any circuit 400 has detected that the integrated voltage $V_{integ}$ exceeds the reference voltage $V_{ref}$. The logic circuitry 450 can include a plurality of OR gates that generate a logic signal (e.g., a "1") if any of the logical outputs corresponds to an overdose condition (i.e., $V_{integ}$ is greater than $V_{ref}$). For example, if the logical output of each discriminator 420 is a "1" if $V_{integ}$ is greater than $V_{ref}$ and a "0" if $V_{integ}$ is less than or equal to $V_{ref}$, logic circuitry 450 outputs a logic signal of "1" if a logical output from any discriminator 420 is a "1."

The logic signal generated by logic circuitry 450 is sent to interlock 460, which interrupts or stops the PBS therapy if the logic signal indicates that the patient has received the maximum acceptable dose (i.e., if $V_{integ}$ is greater than $V_{ref}$ at any pixel). Interlock 460 can include one or more switches or relays that can be activated to interrupt or stop beam source 200 from generating beam 201, thereby preventing radiation overdose to the patient.

In some embodiments, logic circuitry 450 opens interlock 460 when the reset signal is sent from external reset 440 to the integrators 410. This can prevent an error condition in which the control circuitry 40 is erroneously held in reset during patient treatment.

In some embodiments, the circuits 400 are in electrical communication with a computer or other microprocessor-based system (in general, a computer) that allows an operator to monitor the proton beam therapy. For example, the computer can display the inputs to the discriminators 420, for example to illustrate the percentage of the maximum acceptable dose that has been delivered at each pixel location (i.e., the integrated voltage $V_{integ}$ divided by the reference voltage $V_{ref}$). This monitoring can also be used to calibrate or test the control circuitry 400 by applying a known dose to each pixel to verify the response of control circuitry 400 and interlock 460. This monitoring can also be used to calibrate the setting of reference voltage source 430.

In some embodiments, the pixelated detector can have non-uniform pixel sizes. For example, the pixelated detector can have smaller-size pixels, resulting in higher resolution, near the center of the beam scan and larger-size pixels, resulting in lower resolution, near the edge of the beam scan. To account for the different pixel sizes, the effective charge set point can be adjusted by selecting the value of the integrator capacitor in integrator 410 to match the pixel size. Varying the value of the integrator capacitor allows each circuit 400 to use the same global reference voltage 430. In an alternative embodiment, the reference voltage can be customized for each circuit to account for the pixel size, as described below.

Since the local current density (and measured charge delivered to the patient) is a function of pixel size, the reference voltage $V_{ref}$ would need to vary with the pixel size to account for the variation in local current density measurement. Thus, each circuit 600 includes its own reference voltage source 630 and DAC 635.

Figure 5:
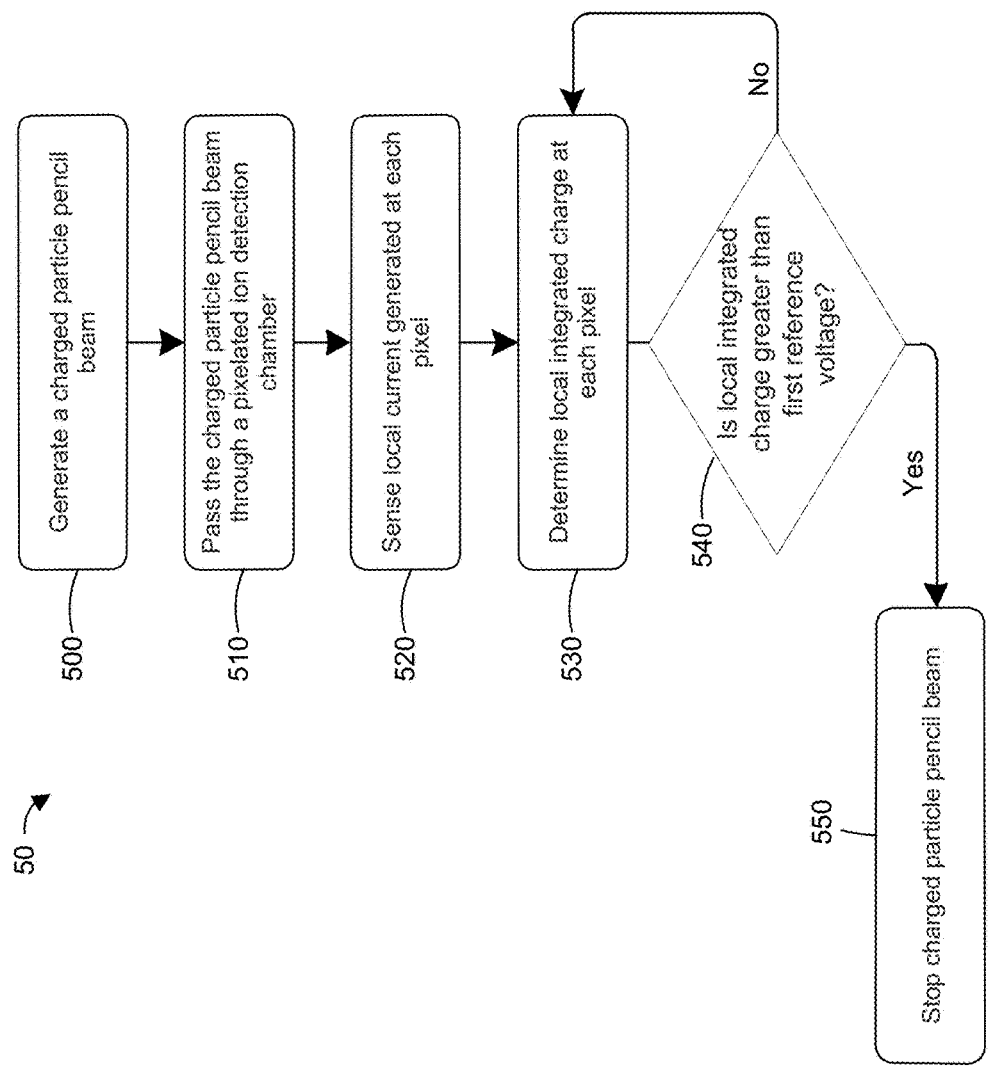
FIG. 5 is a flow chart of a method for preventing patient overdose in PBS therapy according to one or more embodiments.

FIG. 5 is a flow chart 50 of a method for preventing patient overdose in PBS therapy according to one or more embodiments. In step 500, a charged particle pencil beam, such as proton pencil beam, is generated. The charged particle pencil beam can be generated by a proton beam source, such as proton beam source 200 discussed above. In step 510, the beam is passed through a pixelated ion detection chamber, such as pixelated ion detection chamber 230 discussed above. In step 520, the local current at each pixel is sensed. The local current for each pixel can pass through a readout cable to control circuitry (e.g., control circuitry 40) for preventing patient overdose. In step 530, the local integrated charge at each pixel is determined, for example using a current integrator. The local integrated charge is the integral of the local current from a start time (e.g., start of therapy or start of therapy at a particular beam energy level) and can be represented by an integrated voltage $V_{integ}$, as discussed above.

In step 540, the system determines if the integrated voltage $V_{integ}$ is greater than a reference voltage $V_{ref}$ that corresponds to the maximum acceptable dose to the patient. If the integrated voltage $V_{integ}$ is greater than reference voltage $V_{ref}$, the system stops or interrupts the beam and the patient therapy to avoid overdose. If the integrated voltage $V_{integ}$ is less than or equal to the reference voltage $V_{ref}$, the method returns to steps 530 and 540 in a loop to continually or periodically determine the integrated voltage $V_{integ}$ and to determine if the integrated voltage $V_{integ}$ is greater than the reference voltage $V_{ref}$. In this way, the method continually or periodically monitors the PBS therapy to prevent overdose.

As can be seen, the above provides hardware-based systems and methods for preventing overdose to the patient from a PBS. However, it is noted that some or all of the systems and methods can be provided as software or as software in combination with hardware.

Figure 6:
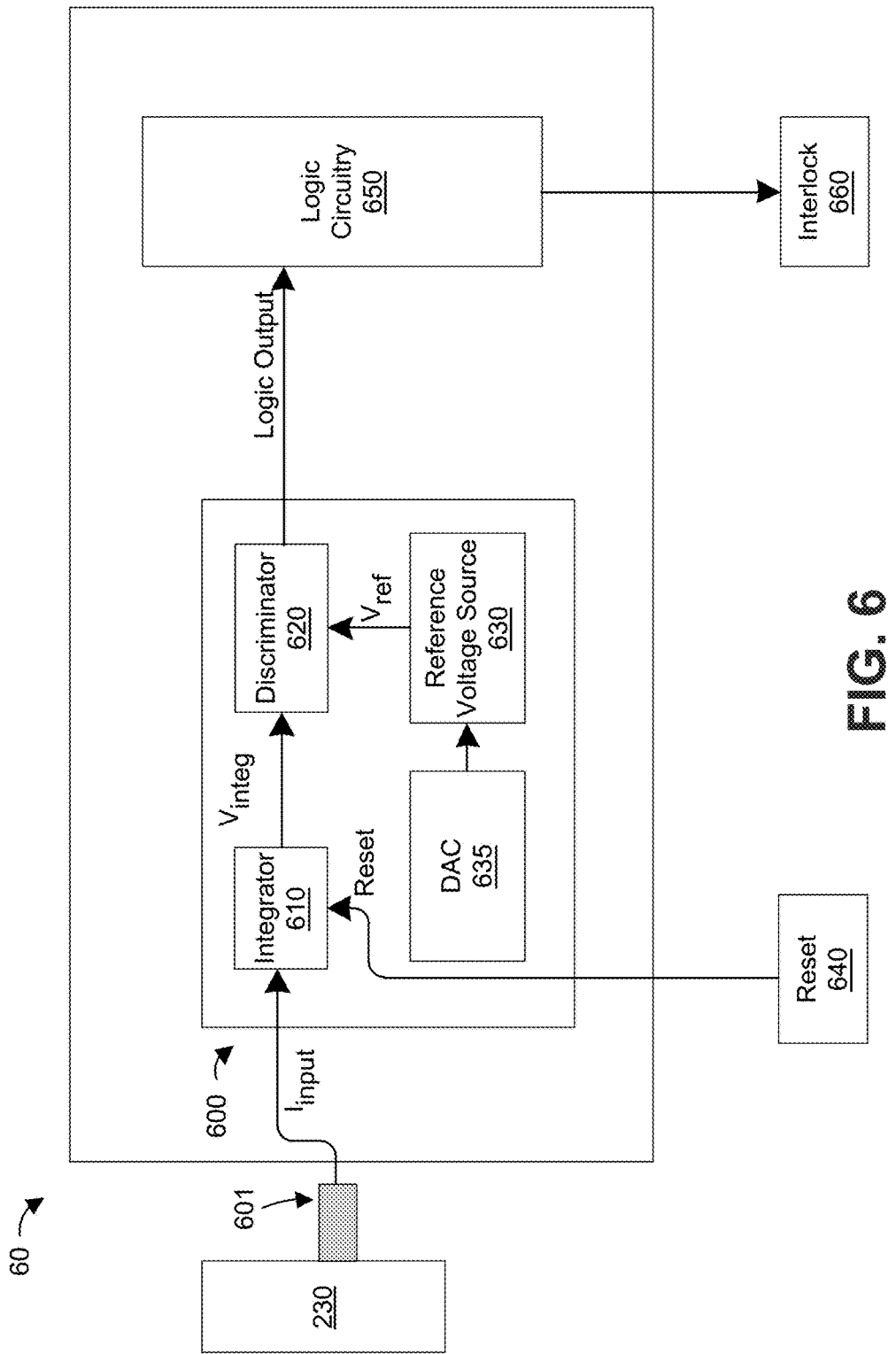
FIG. 6 illustrates control circuitry for preventing patient overdose according to one or more embodiments.

FIG. 6 illustrates control circuitry 60 for preventing patient overdose according to one or more embodiments. Control circuitry 60 includes a plurality of identical or substantially identical circuits 600, each circuit 600 connected via readout cable 601 to a pixel in pixelated ion detector chamber 230. Only a representative circuit 600 is illustrated in FIG. 6 for clarity. Circuit 600 includes an integrator 610, a discriminator 620, a reference voltage source 630, and a programmable digital-to-analog converter (DAC) 635. Integrator 610, discriminator 620, and voltage source 630 are the same or similar to integrator 310, 410, discriminator 320, 420, and voltage source 330, 430 discussed above.

The programmable DAC 650 allows the set point of reference voltage $V_{ref}$ to be customized for each pixel based on the expected dose distribution in the therapy plan. In addition or in the alternative, the programmable DAC 650 allows the set point of reference voltage $V_{ref}$ to be customized based on the size of the corresponding pixel, allowing for pixels of different sizes. For example, the pixelated detector can be arranged to have smaller-size pixels, resulting in higher resolution, near the center of the beam scan and larger-size pixels, resulting in lower resolution, near the edge of the beam scan. Since the local current density (and measured charge delivered to the patient) is a function of pixel size, the reference voltage $V_{ref}$ would need to vary with the pixel size to account for the variation in local current density measurement. Thus, each circuit 600 includes its own reference voltage source 630 and DAC 635, which are referred to collectively as a programmable voltage source.

As in the above examples, the logic output of discriminator 620 is sent to logic circuitry 650, which determines if any of the circuits has detected an overdose (i.e., $V_{integ}$ greater than $V_{ref}$). If so, logic circuit 650 generates an output to interlock 660 to stop or interrupt the pencil beam therapy, thereby preventing overdose to the patient.

In some embodiments, the circuits 600 are in electrical communication with a computer that allows an operator to monitor the proton beam therapy. For example, the computer can display the inputs to the discriminators 620, for example to illustrate the percentage of the maximum acceptable dose that has been delivered at each pixel location (i.e., the integrated voltage $V_{integ}$ divided by the reference voltage $V_{ref}$). This monitoring can also be used to calibrate or test the control circuitry 600 by applying a known dose to each pixel to verify the response of control circuitry 600 and interlock 660. This monitoring can also be used to calibrate the setting of reference voltage source 630.

Figure 7:
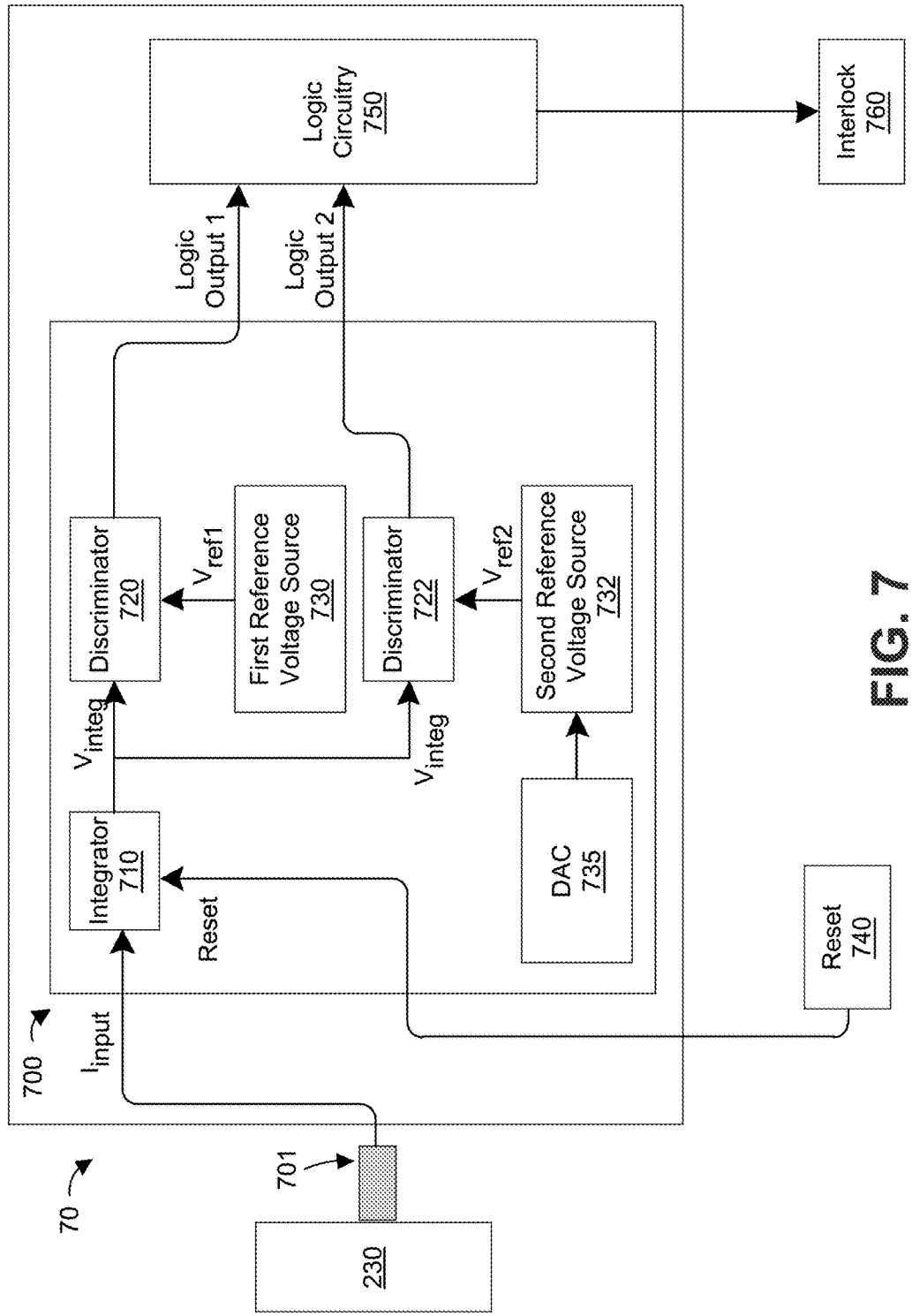
FIG. 7 illustrates control circuitry for preventing patient overdose according to one or more embodiments.

FIG. 7 illustrates control circuitry 70 for preventing patient overdose according to one or more embodiments. Control circuitry 70 includes a plurality of identical or substantially identical circuits 700, each circuit 700 connected via readout cable 701 to a pixel in pixelated ion detector chamber 230. Only a representative circuit 700 is illustrated in FIG. 6 for clarity. Circuit 700 includes an integrator 710 connected in parallel to discriminators 720, 722. Discriminator 720 is connected to integrator 710 and reference voltage source 730. Thus, discriminator 720 receives as inputs $V_{integ}$ and $V_{ref1}$ and generates an output of logical output 1.

Discriminator 722 is connected to integrator 710 and reference voltage source 732, which can be set by DAC 735, similar to the embodiment described in FIG. 6. Reference voltage source 732 and DAC 735 are referred to collectively as a programmable voltage source. Thus, discriminator 722 receives as inputs $V_{integ}$ and $V_{ref2}$ and generates an output of logical output 2. In some embodiments, DAC 735 (and/or DAC 635) can set the reference voltage through an automated process based on the expected dose distribution of the patient's treatment plan.

The use of two discriminators and two logical outputs provides a secondary or backup fault detection to improve the safety of control circuitry 70. For example, reference voltage $V_{ref2}$ can be varied by DAC 735 according to the size of the pixel, the beam energy level, and/or the expected dose distribution of a patient's treatment plan. In contrast, reference voltage $V_{ref1}$ can be a constant reference voltage across each circuit 700 to provide a global maximum acceptable dose limit, which can be set more conservatively or can be a failsafe if $V_{ref2}$ is not calculated correctly. The logic circuitry 750 determines if any of the logic outputs from any of the circuits 700 indicate that the maximum acceptable dose limit has been exceeded (i.e., if $V_{integ}$ is greater than $V_{ref1}$ or $V_{ref2}$).

In some embodiments, the circuits 700 are in electrical communication with a computer that allows an operator to monitor the proton beam therapy. For example, the computer can display the inputs to the discriminators 720, 722 for example to illustrate the percentage of the maximum acceptable dose that has been delivered at each pixel location (i.e., the integrated voltage $V_{integ}$ divided by the corresponding reference voltage $V_{ref1}$, $V_{ref1}$). This monitoring can also be used to calibrate or test the control circuitry 700 by applying a known dose to each pixel to verify the response of control circuitry 700 and interlock 760. This monitoring can also be used to calibrate the setting of each reference voltage source 730, 732.

Figure 8:
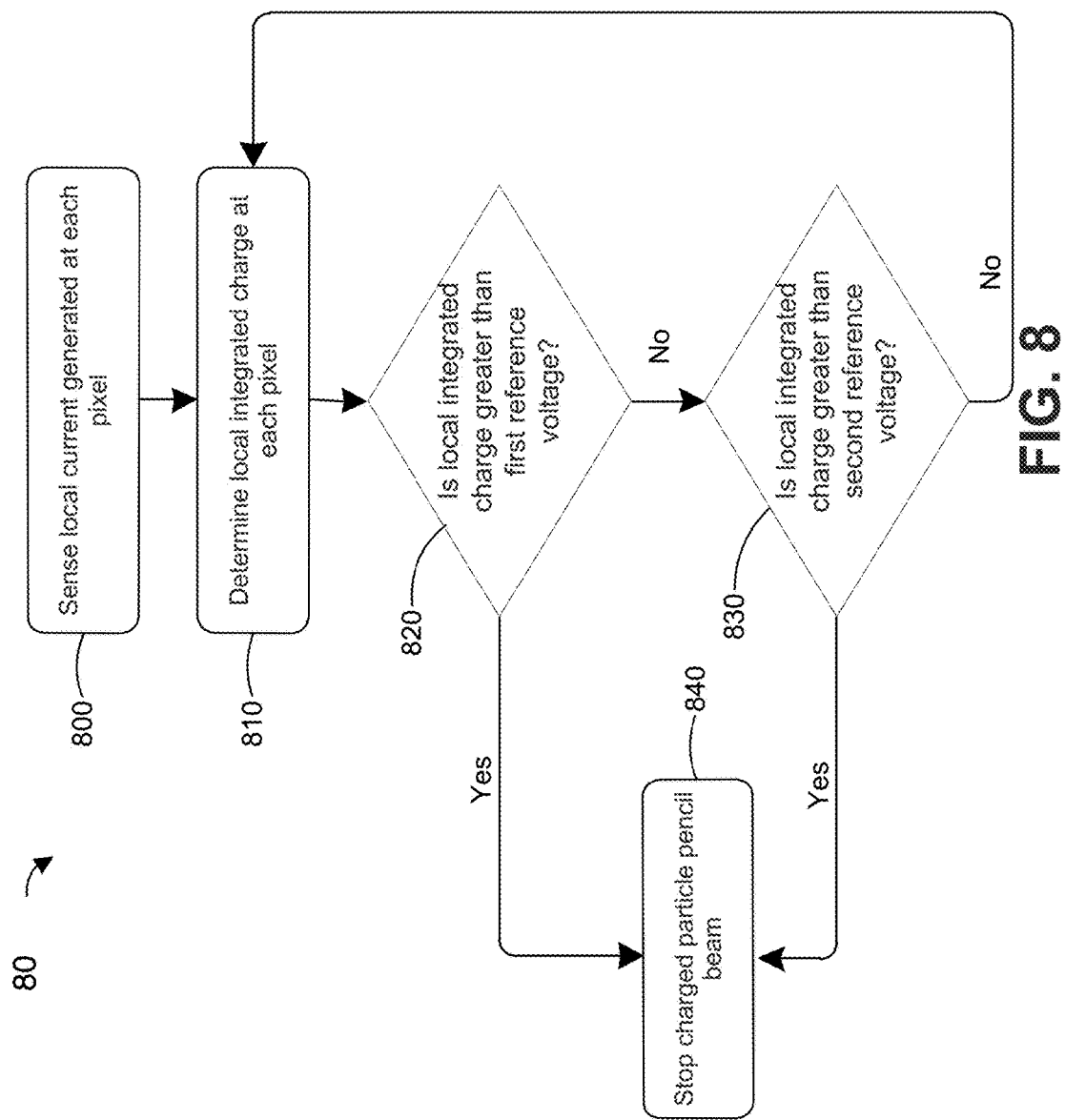
FIG. 8 is a flow chart of a of a method for preventing patient overdose in PBS therapy according to one or more embodiments.

FIG. 8 is a flow chart 80 of a of a method for preventing patient overdose in PBS therapy according to one or more embodiments. In step 800, the local current at each pixel of a pixelated ion detection system is sensed. The local current for each pixel can pass through a readout cable to control circuitry (e.g., control circuitry 70) for preventing patient overdose. In step 810, the local integrated charge at each pixel is determined, for example using a current integrator. The local integrated charge is the integral of the local current from a start time (e.g., start of therapy or start of therapy at a particular beam energy level) and can be represented by an integrated voltage $V_{integ}$, as discussed above.

In step 820, the system determines if the local integrated voltage $V_{integ}$ is greater than a first reference voltage $V_{ref1}$ that corresponds to a global maximum acceptable dose to the patient. If the integrated voltage $V_{integ}$ is greater than reference voltage $V_{ref1}$, the system stops or interrupts the beam at step 840 to avoid overdose. If the integrated voltage $V_{integ}$ is less than or equal to the first reference voltage $V_{ref1}$, the method proceeds to steps 830 to determine if the local integrated voltage $V_{integ}$ is greater than a second reference voltage $V_{ref2}$ that corresponds to a local maximum acceptable dose to the patient, which can be based on the size of the pixel, the beam energy, and/or other factors. If the integrated voltage $V_{integ}$ is greater than reference voltage $V_{ref2}$, the system stops or interrupts the beam at step 840 to avoid overdose. If the integrated voltage $V_{integ}$ is less than or equal to the second reference voltage $V_{ref2}$, the method return to step 810 in a loop to re-determine the integrated voltage $V_{integ}$. The methods continues in this loop until one of the following occurs: (a) the PBS therapy is complete; (b) the PBS therapy at a given energy level is complete and a reset signal is sent to the integrators; or (c) the control circuitry determines that $V_{integ}$ is greater than $V_{ref1}$ or $V_{ref2}$ in steps 820 and 830, which causes the beam to be stopped in step 840.

It is noted that steps 500 and 510, from flow chart 50, are omitted from flow chart 80 to provide a more succinct flow chart. However, these steps can also be practiced in flow chart 80.

While the above paragraphs have described embodiments of the invention with reference to a proton pencil beam, is it noted that the principles described above are applicable to systems using other ionized particles (e.g., helium, carbon, nitrogen, etc.) and for other therapeutic applications, including applications that do not include a pencil beam (e.g., double scattering). In addition, while the above paragraphs include descriptions of hardware circuitry, it is noted that some or all of the functions performed by the hardware circuitry can be implemented using software or a combination of hardware and software. There may be advantageous and/or disadvantageous to implementing the hardware functions in software.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

What is claimed is:

1. An assembly for preventing an overdose of a charged particle beam during therapy to a patient, comprising:
   a detector apparatus comprising detector elements that form a plurality of pixels, the detector apparatus configured to output, for each said pixel, a local measured current corresponding to a local measured intensity of said particle beam at said pixel;
   a controller in communication with said particle beam generator and said detector apparatus, said controller comprising, for each said pixel:
      a current integrator circuit that converts said local measured current into a total local detected charge integrated from a start time, the integrator circuit outputting an integrator voltage that corresponds to said total local detected charge; and
      a discriminator circuit that compares the integrator voltage with a reference voltage, the reference voltage corresponding to a maximum acceptable dose for said patient;
   a logic circuit that generates an overdose fault signal if, at any of said pixels, said integrator voltage is higher than said reference voltage.

2. The system of claim 1, wherein an output of the discriminator circuit comprises a logic output.

3. The system of claim 2, wherein the logic output has a first value when the integrator voltage is less than or equal to the reference voltage and the logic output has a second value when the integrator voltage is greater than the reference voltage.

4. The system of claim 1, further comprising an interlock circuit in communication with the logic circuit, the interlock circuit configured to stop the particle beam generator upon receipt of the overdose fault signal.

5. The system of claim 1, further comprising a reset circuit configured to reset the start time of each current integrator circuit.

6. The system of claim 1, further comprising a programmable reference voltage source that provides the reference voltage.

7. An assembly for preventing an overdose of a charged particle beam during therapy to a patient, comprising:
   a detector comprising detector elements that form a plurality of pixels, the detector apparatus configured to output, for each said pixel, a local measured current corresponding to a local measured intensity of said particle beam at said pixel;
   a controller in communication with said particle beam generator and said detector apparatus, said controller comprising, for each said pixel:
      a current integrator circuit that converts said local measured current into a total local detected charge integrated from a start time, the integrator circuit outputting an integrator voltage that corresponds to said total local detected charge; and
      a first discriminator circuit that compares the integrator voltage with a first reference voltage corresponding to a first maximum acceptable dose for said patient;
      a programmable reference voltage source that outputs a programmable reference voltage corresponding to a second maximum acceptable dose for said patient; and
      a second discriminator circuit that compares the integrator voltage with the programmable reference voltage;
   a logic circuit that generates an overdose fault signal if, at any of said pixels, said integrator voltage is higher than the first reference voltage or the programmable reference voltage.

8. The system of claim 7, wherein said first discriminator circuit for each pixel is in electrical communication with a common first reference voltage source, the common first reference voltage source being common to the first discriminator circuit for each said pixel.

9. The system of claim 7, wherein the programmable reference voltage source includes a programmable digital-to-analog converter.

10. The system of claim 9, wherein the programmable digital-to-analog converter sets the programmable reference voltage according to a size of the pixel.

11. The system of claim 9, wherein the programmable digital-to-analog converter sets the programmable reference voltage according to a treatment plan.

12. The system of claim 7, wherein an output of the first discriminator circuit comprises a first logic output and output of the second discriminator circuit comprises a second logic output.

13. The system of claim 12, wherein:
   the first logic output has a first value when the integrator voltage is less than or equal to the first reference voltage and the first logic output has a second value when the integrator voltage is greater than the first reference voltage, and
   the second logic output has a first value when the integrator voltage is less than or equal to the second reference voltage and the second logic output has a second value when the integrator voltage is greater than the second reference voltage.

14. The system of claim 1, further comprising an interlock circuit in communication with the logic circuit, the interlock circuit configured to stop the particle beam generator upon receipt of the overdose fault signal.

15. The system of claim 14, wherein the interlock circuit includes a relay.

16. The system of claim 1, further comprising a reset circuit configured to reset the start time of each current integrator circuit.

17. A method of preventing an overdose of a charged particle beam during therapy to a patient, the method comprising:
   passing the charged particle pencil beam through a pixelated ion detector chamber comprising detector elements that form a plurality of pixels;
   for each said pixel,
      receiving a local measured current collected at said pixel;
      passing said local measured current through a current integrator circuit that converts said local measured current into an integrator voltage that corresponds to a total local detected charge integrated from a start time;
      comparing the integrator voltage with a reference voltage that corresponds to a maximum acceptable dose for said patient; and
      stopping the therapy if the integrator voltage is greater than the reference voltage.

18. The method of claim 17, further comprising automatically setting the reference voltage according to a treatment plan.

19. The method of claim 18, further comprising comparing the integrator voltage with a second reference voltage that corresponds to a second maximum acceptable dose for said patient.

20. The method of claim 19, wherein the second reference voltage is a common reference voltage.

* * * * *